United States Patent
Lee et al.

(10) Patent No.: US 11,957,667 B2
(45) Date of Patent: Apr. 16, 2024

(54) INHIBITORS OF POSITIVE STRAND RNA VIRUSES

(71) Applicant: National Health Research Institutes, Miaoli County (TW)

(72) Inventors: Shiow-Ju Lee, Miaoli County (TW); Cheng-Wei Yang, Miaoli County (TW); Yue-Zhi Lee, Miaoli County (TW); Hsing-Yu Hsu, Miaoli County (TW)

(73) Assignee: National Health Research Institutes, Miaoli County (TW)

( * ) Notice: Subject to any disclaimer, the term of this patent is extended or adjusted under 35 U.S.C. 154(b) by 293 days.

(21) Appl. No.: 17/369,589

(22) Filed: Jul. 7, 2021

(65) Prior Publication Data

US 2022/0008399 A1    Jan. 13, 2022

Related U.S. Application Data

(60) Provisional application No. 63/049,140, filed on Jul. 8, 2020.

(51) Int. Cl.
| | | |
|---|---|---|
| *A61K 31/437* | (2006.01) | |
| *A61K 31/4375* | (2006.01) | |
| *A61K 31/473* | (2006.01) | |
| *A61P 31/14* | (2006.01) | |

(52) U.S. Cl.
CPC ........ *A61K 31/437* (2013.01); *A61K 31/4375* (2013.01); *A61K 31/473* (2013.01); *A61P 31/14* (2018.01)

(58) Field of Classification Search
None
See application file for complete search history.

(56) References Cited

U.S. PATENT DOCUMENTS

| | | |
|---|---|---|
| 7,652,027 B2 | 1/2010 | Lee et al. |
| 8,440,649 B2 | 5/2013 | Lee et al. |
| 8,486,959 B2 | 7/2013 | Lee et al. |
| 9,216,977 B2 | 12/2015 | Lee et al. |
| 2011/0201637 A1 | 8/2011 | Ikeda et al. |

FOREIGN PATENT DOCUMENTS

| | | |
|---|---|---|
| TW | I430794 B | 3/2014 |
| TW | I436983 B | 5/2014 |

OTHER PUBLICATIONS

Fernandes et al, Viruses, 12, 598, pp. 1-22, May 30 (Year: 2020).*
Lee et al, Journal of Medicinal Chemistry, vol. 55, No. 23, pp. 10363-10377 (Year: 2012).*
Cyriac et al "Tylophorine: Sources, Properties, Applications and Biotechnological Production" Plant-Derived Bioactives, pp. 167-176, 2020.
Nazar et al "Alkaloid-Rich Plant Tylophora Indica; Current Trends in Isolation Strategies, Chemical Profiling and Medicinal Applications" Arabian Journal of Chemistry vol. 13, pp. 6348-6365, 2020.
Yang et al "Identification of Phenanthroindolizines and Phenanthroquinolizidines as Novel Potent Anti-Coronaviral Agents for Porcine Enteropathogenic Coronavirus Transmissible Gastroenteritis Virus and Human Severe Acute Respiratory Syndrome Coronavirus" Antiviral Research vol. 88, pp. 160-168, 2010.
Yang et al "Inhibition of SARS-COV-2 by Highly Potent Broad-Spectrum Anti-Coronaviral Tylophorine-Based Derivatives" Frontiers in Pharmacology vol. 11, pp. 1-12, 2020.

* cited by examiner

*Primary Examiner* — Zinna Northington Davis
(74) *Attorney, Agent, or Firm* — Morse, Barnes-Brown & Pendleton, P.C.; Martin Z. Zhang, Esq.

(57) ABSTRACT

Methods of treating a disease caused by a positive strand RNA virus. The methods include administering to a subject in need thereof an effective amount of a compound of Formula I or Formula II.

3 Claims, 1 Drawing Sheet

INHIBITORS OF POSITIVE STRAND RNA VIRUSES

CROSS-REFERENCE TO RELATED APPLICATIONS

This application claims the benefit of priority based on U.S. Provisional Application No. 63/049,140, filed Jul. 8, 2020, the entire content and disclosure of which is incorporated herein by reference in its entirety.

BACKGROUND

Positive strand RNA viruses include pathogens such as Zika virus, Dengue virus, human coronavirus OC43 ("HCoV-OC43"), human coronavirus 229E ("HCoV-229E"), and severe acute respiratory syndrome coronavirus 2 ("SARS-CoV-2").

Zika virus caused the widespread epidemic of Zika fever in 2015 and 2016. It can be transmitted from a pregnant woman to her fetus, causing microcephaly and other severe brain anomalies in infants. Currently, there is no specific medicine or vaccine for Zika virus.

Dengue virus spreads through the bite of an infected *Aedes* species mosquito, causing Dengue fever. It is common in more than 100 countries and infects millions of people worldwide each year. Only one vaccine, i.e., Dengvaxia®, has been approved so far for people who have already had dengue fever at least once. Preventing mosquito bites and controlling mosquito population remain the main methods for fighting Dengue virus.

HCoV-OC43 and HCoV-229E, viruses responsible for the common cold, are associated with upper respiratory tract infections. They can also cause severe lower respiratory tract illnesses, including bronchiolitis, bronchitis, croup, and pneumonia, primarily in infants and immunocompromised patients. Medicines are available only to reduce pain and fever. Vaccines have not been commercialized to protect people against these two human coronaviruses.

SARS-CoV-2 caused the COVID-19 pandemic, leading to more than 3.9 million of deaths worldwide. To contain the spread of the pandemic, many countries implemented year-long non-pharmaceutical interventions such as stay-at-home orders, curfews, and quarantines, sending the global economy into a recession. The US Food and Drug Administration has approved one medicine, remdesivir, to treat COVID-19. Studies show that remdesivir is effective in only a small portion of patients, allowing them to recover faster. Other potential treatments include repurposed medicines, e.g., baricitinib, dexamethasone, ciclesonide, chloroquine, and hydroxychloroquine. None of the treatments has high efficacy.

There is an unmet need to develop an efficient treatment for infections caused SARS-CoV-2, Dengue virus, Zika virus, HCoV-OC43, and HCoV-229E. Particularly, a potent treatment for COVID-19 is urgently demanded.

SUMMARY

To address the above need, certain compounds have been identified that surprisingly inhibit positive strand RNA viruses including Dengue virus, Zika virus, HCoV-OC43, HCoV-229E, and SARS-CoV-2.

Accordingly, one aspect of this invention relates to a method of treating a disease caused by a positive strand RNA virus. The method includes the steps of identifying a subject suffering from the disease and administering to the subject an effective amount of a compound of Formula I below:

Formula I

In this formula, (1) each of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$, independently, is H, halo, alkyl, aryl, cycloalkyl, heteroaryl, heterocycloalkyl, OH, alkoxy, carbonyloxy, or amino; (2) each of $R_{16}$ and $R_{17}$, independently, is H, halo, alkyl, aryl, cycloalkyl, heteroaryl, heterocycloalkyl, OH, alkoxy, carbonyloxy, or amino, or $R_{16}$ and $R_{17}$ together are a single bond; (3) each of ≈≈≈ and ≈≈≈, independently, is a single bond or a double bond; and (4) n is 1, 2 or 3. When ≈≈≈ between X and Y is a single bond, X is C=O or CR'R" and Y is N or $N^+ \to O^-$, in which each of R' and R", independently, is H, halo, alkyl, aryl, cycloalkyl, heteroaryl, heterocycloalkyl, OH, alkoxy, or amino. When ≈≈≈ between X and Y is a double bond, X is CR', Y is N+, and a counterion coexists in the compound, R' being defined above.

Preferably, each of $R_1$, $R_5$, $R_8$, $R_9$, $R_{10}$, $R_{11}$, $R_{12}$, $R_{13}$, $R_{14}$, and $R_{15}$ is H; each of $R_2$, $R_3$, $R_6$, and $R_7$, independently, is alkoxy (e.g., $C_1$-$C_6$ alkoxy, methoxy, and ethoxy); $R_4$ is H or alkoxy (e.g., $C_1$-$C_6$ alkoxy, methoxy, and ethoxy); $R_{16}$ and $R_{17}$ together are a single bond; X is $CH_2$; and Y is N or N+→O−; each of ≈≈≈ and ≈≈≈ is a single bond; and n is 1 or 2.

The structures of three exemplary compounds of Formula I, i.e., Compound 1, Compound 4, and Compound 6, shown below:

-continued

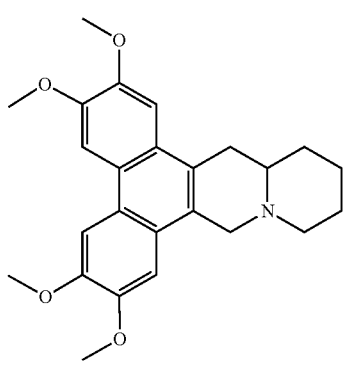

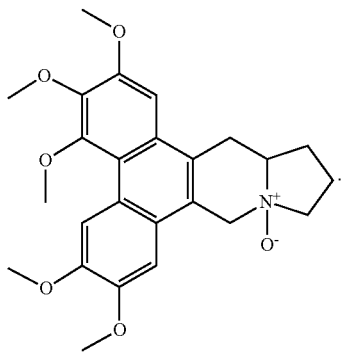

The positive strand RNA virus can be a flavivirus (e.g., Zika virus, Dengue virus) or a coronavirus (e.g., SARS-CoV-2, HCoV-OC43, and HCoV-229E).

Another aspect of this invention relates to a treatment method including the steps of identify a subject having a disease caused by a positive strand RNA virus and administering to the subject an effective amount of a compound of Formula II:

Formula II

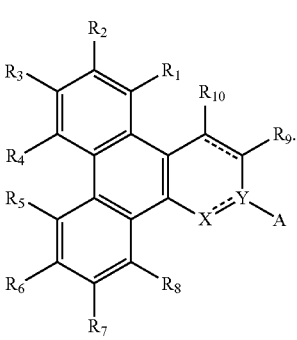

In this formula, (1) each of $R_1$, $R_2$, $R_3$, $R_4$, $R_5$, $R_6$, $R_7$, $R_8$, $R_9$, and $R_{10}$, independently, is H, alkyl, alkenyl, alkynyl, cycloalkyl, heterocycloalkyl, aryl, heteroaryl, halo, nitro, cyano, —$OR^a$, —$OC(O)R^a$, —$C(O)OR^a$, —$NR^aR^b$, —$NR^aC(O)R^b$, or —$C(O)NR^aR^b$, each of $R^a$ and $R^b$, independently, being H, alkyl, aryl, heteroaryl, cycloalkyl, or hetercycloalkyl; (2) X⸺Y, together, is C(R')(R")—N or CR'=$N^+$, in which R' is H, alkyl, alkenyl, alkynyl, cycloalkyl, heterocycloalkyl, aryl, heteroaryl, halo, nitro, or cyano, and R" is H, alkyl, alkenyl, alkynyl, cycloalkyl, heterocycloalkyl, aryl, heteroaryl, halo, nitro, cyano, —$OR^c$, or —$OC(O)R^c$, $R^c$ being H, alkyl, aryl, heteroaryl, cycloalkyl, or hetercycloalkyl; (3) A is H, alkyl, alkenyl, alkynyl, cycloalkyl, heterocycloalkyl, aryl, or heteroaryl; and (4) ⸺ is a single bond or a double bond.

Preferably, each of $R_1$, $R_4$, $R_5$, and $R_8$ is H; $R_2$ is H or alkoxy (e.g., $C_1$-$C_6$ alkoxy, methoxy, and ethoxy); each of $R_3$, $R_6$, and $R_7$, independently, is alkoxy (e.g., $C_1$-$C_6$ alkoxy, methoxy, and ethoxy); $R_9$ is H or alkyl (e.g., $C_1$-$C_6$ alkyl, methyl, ethyl, propyl, and isopropyl), $R_{10}$ is H or OH; X is $CH_2$; Y is N; A is alkyl (e.g., $C_1$-$C_6$ alkyl, methyl, ethyl, propyl, and isopropyl); and ⸺ is a single bond.

Exemplary compounds of Formula II include Compounds 2, Compound 3, Compound 5, Compound 7, Compound 8, and Compound 9, the structures of which follow:

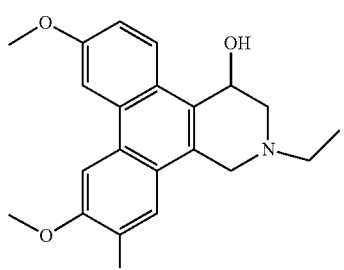

2

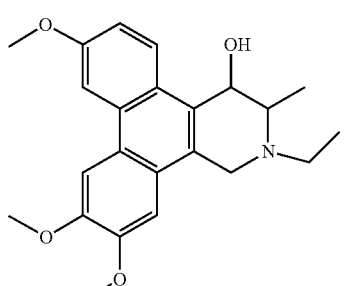

3

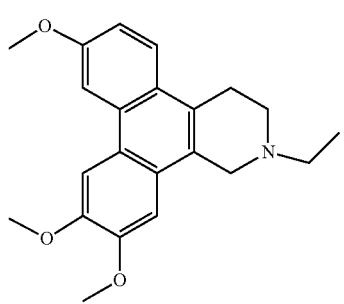

5

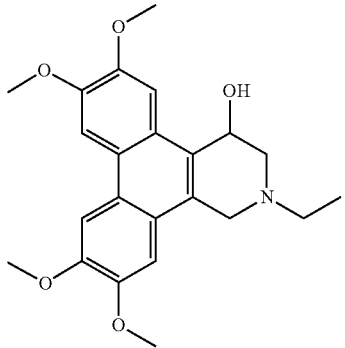

7

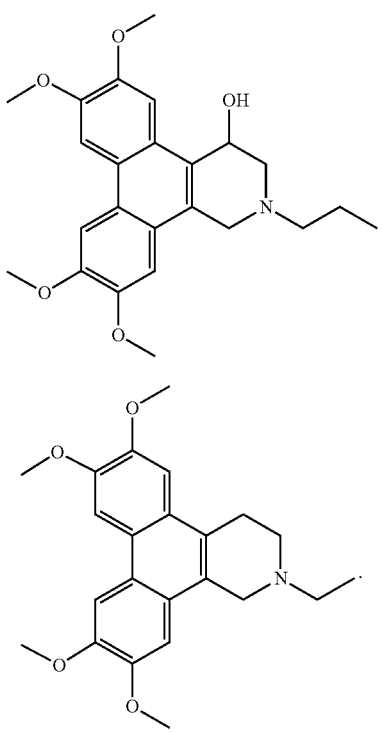

The term "alkyl" herein refers to a straight or branched hydrocarbon group, containing 1-20 (e.g., 1-10 and 1-6) carbon atoms. Examples include methyl, ethyl, n-propyl, i-propyl, n-butyl, i-butyl, and t-butyl. Alkyl includes its halo substituted derivatives, i.e., haloalkyl, which refers to alkyl substituted with one or more halogen (chloro, fluoro, bromo, or iodo) atoms. Examples include trifluoromethyl, bromomethyl, and 4,4,4-trifluorobutyl. The term "alkoxy" refers to an —O-alkyl group. Examples include methoxy, ethoxy, propoxy, and isopropoxy. Alkoxy includes haloalkoxy, referring to alkoxy substituted with one or more halogen atoms. Examples include —O—CH$_2$Cl and —O—CHClCH$_2$Cl.

The term "cycloalkyl" refers to a saturated and partially unsaturated monocyclic, bicyclic, tricyclic, or tetracyclic hydrocarbon group having 3 to 12 carbons. Examples of cycloalkyl groups include, but are not limited to, cyclopropyl, cyclobutyl, cyclopentyl, cyclopentenyl, cyclohexyl, cyclohexenyl, cycloheptyl, and cyclooctyl.

The term "heterocycloalkyl" refers to a nonaromatic 5-8 membered monocyclic, 8-12 membered bicyclic, or 11-14 membered tricyclic ring system having one or more heteroatoms (e.g., O, N, P, and S). Examples of heterocycloalkyl groups include, but are not limited to, piperazinyl, imidazolidinyl, azepanyl, pyrrolidinyl, dihydrothiadiazolyl, dioxanyl, morpholinyl, tetrahydropuranyl, and tetrahydrofuranyl.

The term "aryl" refers to a 6-carbon monocyclic, 10-carbon bicyclic, 14-carbon tricyclic aromatic ring system wherein each ring may have 1 to 5 substituents. Examples of aryl groups include phenyl, naphthyl, and anthracenyl. The term "arylene" refers to bivalent aryl. The term "aralkyl" refers to alkyl substituted with an aryl group.

The term "heteroaryl" refers to an aromatic 5-8 membered monocyclic, 8-12 membered bicyclic, or 11-14 membered tricyclic ring system having one or more heteroatoms (e.g., O, N, P, and S). Examples include triazolyl, oxazolyl, thiadiazolyl, tetrazolyl, pyrazolyl, pyridyl, furyl, imidazolyl, benzimidazolyl, pyrimidinyl, thienyl, quinolinyl, indolyl, thiazolyl, and benzothiazolyl. The term "heteroaryl alkyl" refers to an alkyl group substituted with a heteroaryl group.

The terms "halo" refers to a fluoro, chloro, bromo, or iodo radical. The term "amino" refers to a radical derived from amine, which is unsubstituted or mono-/di-substituted with alkyl, aryl, cycloalkyl, heterocycloalkyl, or heteroaryl. The term "alkylamino" refers to alkyl-NH—. The term "dialkylamino" refers to alkyl-N(alkyl)-.

Alkyl, cycloalkyl, heterocycloalkyl, aryl, heteroaryl, aralkyl, heteroaralkyl, alkoxy, and aryloxy mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cycloalkyl, and heterocycloalkyl, in which alkyl, alkenyl, alkynyl, alkyloxy, aryl, heteroaryl cycloalkyl, and heterocycloalkyl may further substituted.

Compounds of Formula I or Formula II can include an anion. Examples of an anion include Cl$^-$, Br$^-$, I$^-$, SO$_4^{2-}$, PO$_4^{3-}$, ClO$_4^-$, CH$_3$CO$_2^-$, and CF$_3$CO$_2^-$.

The term "compound", when referring to a compound of Formula I or Formula II, also covers its salts, solvates, and prodrugs. A salt can be formed between an anion and a positively charged group (e.g., amino) on a compound; examples of a suitable anion include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. A salt can also be formed between a cation and a negatively charged group; examples of a suitable cation include sodium ion, potassium ion, magnesium ion, calcium ion, and an ammonium cation such as tetramethylammonium ion. Further, a salt can contain quaternary nitrogen atoms. A solvate refers to a complex formed between an active compound and a pharmaceutically acceptable solvent. Examples of a pharmaceutically acceptable solvent include water, ethanol, isopropanol, ethyl acetate, acetic acid, and ethanolamine. A prodrug refers to a compound that, after administration, is metabolized into a pharmaceutically active drug. Examples of a prodrug include esters and other pharmaceutically acceptable derivatives, which, upon administering to a subject, are capable of providing active compounds of this invention.

The details of the invention are set forth in the drawings, the definitions, and the detailed description below. Other features, objects, and advantages of the invention will be apparent from the following actual examples and claims.

BRIEF DESCRIPTION OF THE DRAWING

The description below refers to the accompanying drawing.

DETAILED DESCRIPTION OF THE INVENTION

Figure 1:
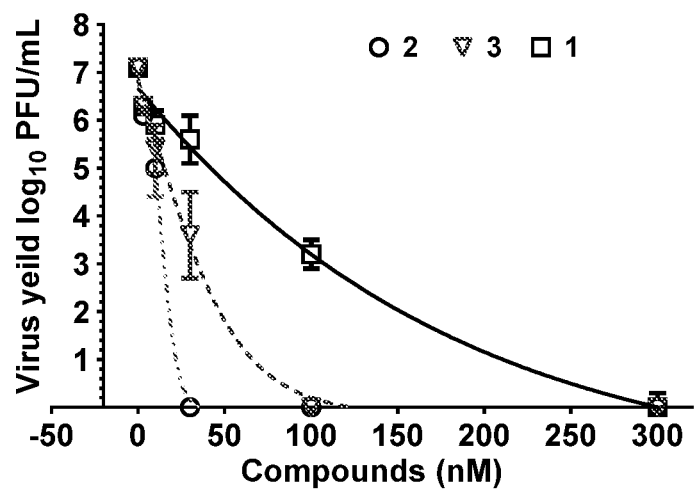
FIG. 1 shows antiviral activities against HCoV-OC43 by three tylophorine compounds, i.e., Compounds 1-3, at concentrations in the range of 0 to 300 nM.
Figure 2:
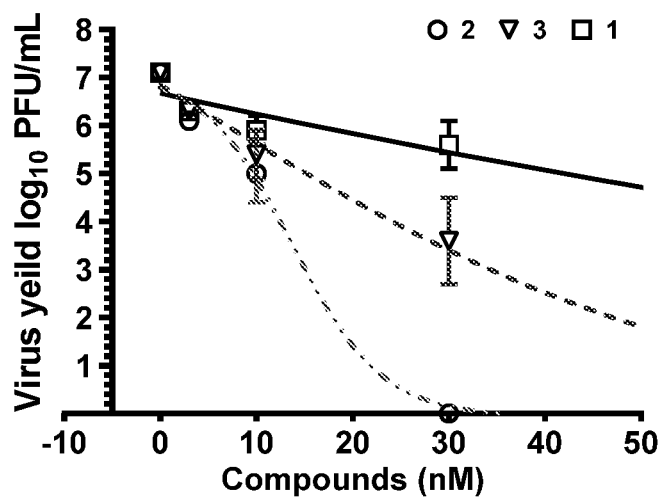
FIG. 2 shows antiviral activities against HCoV-OC43 by Compounds 1-3 at concentrations in the range of 0 to 50 nM.

As disclosed above, tylophorine (i.e., Compound 1) and its derivatives are used to treat diseases caused by a positive strand RNA virus.

Tylophorine, $C_{24}H_{27}NO_4$, is a major alkaloid contained in roots and leaves of *Tylophora indica*, a climbing plant originally established in the eastern and southern India. *Tylophora indica* is widely used in folk medicines for allergies, asthma, cancers, coughing, joint disorders (rheumatoid arthritis), etc.

Tylophorine was first extracted from the plant as early as 1935. See Ratnagiriswaran et al., *Indian J. Med. Res.* 22(3), 433-441 (1935). Biologically efficacious tylophorine was extracted from *Tylophora indica* by acid extraction and solvent distillation utilizing methanol, ethyl acetate, and chloroform almost four decades later. See Rao et al., *F. J. Pharma. Sci.* 60(11), 1725-26 (1971). The structure of tylophorine was elucidated by different spectroscopic techniques. See Govindachari et al., *Proc. Indian Acad. Sci.* 3, 114 (2002). Tylophorine, having a molecular weight of 393.48, is a secondary metabolite containing organonitrogen heterocyclic and organic heteropentacyclic compounds. Its IUPAC name is (13as)-2,3,6,7-tetramethoxy-9,11,12,13,13a,14-hexahydrophenanthro[9,10-f]indolizine. See the Summary section above for its chemical structure.

Tylophorine possesses several properties, such as immunosuppressive, antitumor, antifeedant, antibacterial, antifungal, antiamoebic, diuretic and hepatoprotective activities. In addition, it provides positive stimulation to adrenal cortex.

Biotechnological production of tylophorine is fulfilled by inducing hairy roots mediated by *Agrobacterium rhizogenes* (A4 strain). Chemical synthesis of tylophorine, on the other hand, can be achieved using a five-step process via a nitrile stabilized ammonium intermediate. See Lahm et al., *J. Org. Chem.* 77, 6620-23 (2012). Tylophorine is commercially available as yellow solid. Suppliers include Alfa Chemistry (Ronkonkoma, New York), Glixx Laboratories Inc. (Hopkinton, Massachusetts), and MedKoo Biosciences Inc. (Morrisville, North Carolina).

Tylophorine and its derivatives have been used for treating cancers and other disorders. See U.S. Pat. Nos. 7,652,027, 9,216,977 and 8,486,959, and US Patent Application Publication 2011/0201637. Derivatives are typically prepared via chemical syntheses. See, e.g., U.S. Pat. No. 8,486,959, US Patent Application Publication 2011/0201637, Yang et al., *Antiviral Res.* 88, 160-168 (2010); and Lee et al., *J. Med. Chem.* 55, 10363-77 (2012).

Compounds of Formula I or Formula II can be prepared by conventional methods, e.g., procedures provided in the references cited above. Their antiviral activities are then evaluated using known methods such as those described in actual examples below.

Some compounds of this invention contain a non-aromatic double bond or one or more asymmetric centers. Each of them occurs as a racemate or a racemic mixture, a single R enantiomer, a single S enantiomer, an individual diastereomer, a diastereometric mixture, a cis-isomer, or a trans-isomer. Compounds of such isomeric forms are within the scope of this invention. They can be present as a mixture or can be isolated using chiral synthesis or chiral separation technologies.

A compound of Formula I or Formula II is preferably formulated into a pharmaceutical composition containing a pharmaceutical carrier. The composition is then given to a subject in need thereof to treat a Cisd2-insufficient associated disorder or protect against doxorubicin-induced cardiotoxicity.

To practice the method of the present invention, a composition having one or more of the above-described tylophorine compounds can be administered parenterally, orally, nasally, rectally, topically, or buccally.

The term "parenteral" as used herein encompasses subcutaneous, intracutaneous, intravenous, intraperitoneal, intramuscular, intraarticular, intraarterial, intrasynovial, intrasternal, intrathecal, intralesional, and intracranial injection of a sterile injectable composition. Indeed, the term refers to any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or di-glycerides). Fatty acid, such as oleic acid and its glyceride derivatives are useful in the preparation of injectables, as are natural pharmaceutically acceptable oils, such as olive oil and castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens and Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. Oral solid dosage forms can be prepared by spray dried techniques; hot melt extrusion strategy, micronization, and nano milling technologies.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having an active compound can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples of other carriers include colloidal silicon oxide, magnesium stearate, cellulose, sodium lauryl sulfate, and D&C Yellow #10.

The term "treating" refers to application or administration of the compound to a subject with the purpose to cure, alleviate, relieve, alter, remedy, improve, or affect the disease, the symptom, or the predisposition. "An effective amount" refers to the amount of the compound which is required to confer the desired effect on the subject. Effective amounts vary, as recognized by those skilled in the art, depending on route of administration, excipient usage, and the possibility of co-usage with other therapeutic treatments such as use of other active agents. Dosage levels of a compound of Formula I or Formula II are of the order of 0.01 mg/kg body weight to 500 mg/kg body weight (e.g., 0.05 mg/kg body weight to 300 mg/kg body weight, 0.1 mg/kg body weight to 200 mg/kg body weight, and 1 mg/kg body weight to 100 mg/kg body weight) per day. The specific dose level for a particular patient will depend upon a number of factors including age, body weight, general health, sex, diet, time of administration, rate of excretion, and the severity of the disorder. To enhance the therapeutic efficiency, the compound can be administered concomitantly with one or more of other orally active antiviral compounds.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever.

All publications, including patent documents, cited herein are incorporated by reference in their entirety.

EXAMPLES

Tylophorine and eight tylophorine derivatives, i.e., Compounds 1-9, were tested and unexpectedly showed antiviral activities against positive single stranded RNA viruses, i.e., SARS-CoV-2, HCoV-OC43, HCoV-229E, Zika virus, and Dengue virus.

Example 1: Inhibition of SARS-CoV-2

An immunofluorescence assay ("IFA") and a plaque assay were performed to evaluate inhibition of SARS-CoV-2.

SARS-CoV-2 Immunofluorescence Assay

Vero E6 cells derived from BCRC #60476 (Bioresource Collection and Research Center, Hsinchu, Taiwan) were treated with each compound at an indicated concentration for 1 hour at 37° C. The cells were adsorbed with SARS-CoV-2 viruses (TCDC #4, National Taiwan University, Taipei, Taiwan, ROC) at multiplicity of infection ("MOI") of 0.01 for 1 hour at 37° C. After virus adsorption, the cells were washed with phosphate-buffered saline ("PBS"). A fresh medium containing the compound was added at an indicated concentration. The resultant mixture was incubated for 2 days. The cells were fixed with 4% paraformaldehyde and permeabilized with a 0.5% Triton™ X-100 detergent solution (Thermo Fisher Scientific, Waltham, MA). Subsequently, they were stained with an anti-SARS-CoV-2 N protein antibody and anti-human IgG-488 (in green). The nuclei of the cells were counter stained with 4',6-diamidino-2-phenylindole ("DAPI", Thermo Fisher Scientific, MA, USA). The N protein expression was measured using a high-content image analysis system (Molecular Devices, San Jose, CA). The cell viability was determined by Cell Counting Kit-8 (Sigma-Aldrich, St. Louis, MO) $EC_{50}$ and $CC_{50}$ values were calculated by Prism software. The term "$EC_{50}$" refers to the half maximal effective concentration of a compound at which a virus is inhibited by 50%. The term "$CC_{50}$" refers to the 50% cytotoxic concentration of a compound at which the cell viability is reduced by 50%. Both $EC_{50}$ and $CC_{50}$ are measured in molar units, e.g., mol/L ("M"), μmol/L ("μM"), and nmol/L ("nM").

The results are shown in Table 1 below. Compounds 1, 2, and 3 each had a high inhibitory activity against SARS-CoV-2, having a very low $EC_{50}$ in the range of 9 nM to 77 nM.

SARS-CoV-2 Plaque Assay

The assay was performed in triplicate in 24-well tissue culture plates. Vero E6 cells were seeded in Dulbecco's modified Eagle's medium ("DMEM") with 10% Fetal Bovine Serum ("FBS", Biological Industries, Kibbutz, Israel) and antibiotics one day before infection. SARS-CoV-2 viruses were added to the cell monolayer and allowed to sit for 1 hour at 37° C. After viruses were removed, the cell monolayer was washed once with PBS before covering with media containing agarose or methylcellulose for 5-7 days. The cells were fixed with 3.7% formaldehyde overnight followed by removal of overlay media. They were then stained with crystal violet to count the plaque-forming units ("PFU"). The percentage of inhibition was calculated as $[1-(V_D/V_C)]\times 100\%$, where $V_D$ and $V_C$ refer to the virus titer in the presence and absence of a test compound, respectively.

Inhibition of SARS-CoV-2

Compounds 1-3 were examined for their inhibitory activity against SARS-CoV-2 in Vero E6 cells. Cytopathic effects ("CPE") of SARS-CoV-2 infected Vero E6 cells, with treatment of compounds in 2-fold dilution at a series of 12 concentrations, were visualized. $EC_{50}$ and $CC_{50}$ values were calculated. See Table 1 below.

TABLE 1

| SARS-CoV-2 inhibition $EC_{50}$ (nM) | | | | | |
|---|---|---|---|---|---|
| Compound | CPE | IFA-1 | IFA-2 | Plaque assay-1 | Plaque assay-2 |
| 1 | 78 | 64 | 76.8 | nd | nd |
| 2 | 2.5 | 9.1 | 13.9 | 10.8 | 13.8 |
| 3 | 20 | 31.6 | 31.9 | nd | nd |

CPE: cytopathic effect by visualization.

Compounds 1-3 each had a high anti-SARS-CoV-2 activity as shown by the CPE results. In addition, the IFA assay showed results comparable to those from the CPE results. Surprisingly, Compounds 1-3 each had a high potency of inhibiting SARS-CoV-2. Among them, Compound 2 had the highest antivirus activity. The plaque assay was performed four times to measure the potency of Compound 2 against SARS-CoV-2 in infected Vero E6 cells. In all four measurements, Compound 2 had an $EC_{50}$ value in the range of 11~14 nM, which was in consistence with those obtained from the cytopathic effect assay and the IFA assay shown in Table 1 above.

Example 2: Inhibition of HCoV-OC43

Compounds 1-6 were tested for their inhibitory activities against human coronavirus HCoV-OC43 (*Betacoronavirus*) using an IFA assay, which targeted HCoV-OC43 nucleocapsid ("N") protein.

Human colon adenocarcinoma cell line HCT-8 (ATCC® CCL-244™, American Type Culture Collection, Manassas, VA, USA) was obtained from American Type Culture Collection ("ATCC"). It was established as stock at early passage to ensure cell line-specific characteristics. HCoV-OC43 viruses (ATCC® VR1558™, American Type Culture Collection, Manassas, VA, USA) were grown and propagated in HCT-8 cells cultured with DMEM and 2% FBS (Biological Industries, Kibbutz, Israel). The cells were seeded in a 96-well plate and then cultured in a DMEM medium containing 2% FBS. Subsequently, they were pretreated with one of Compounds 1-6 at one of five predetermined concentrations in a 5-fold dilution for 1 hour prior to HCoV-OC43 virus infection at an MOI of 0.05. The resultant supernatant at the 72 d.p.i. were subjected to an endpoint assay and a TCID50 determination after 6 days to measure viral-yield inhibition. The cells (72 d.p.i.) were fixed with 80% acetone and were analyzed by an IFA assay using an antibody against HCoV-OC43 N protein. $EC_{50}$ were determined accordingly. The viabilities of HCT-8 cells were also studied using CellTiter 96® AQueous Non-Radioactive Cell Proliferation Assay kit ("MTS") (Promega, Madison, WI, USA). $CC_{50}$ values were calculated. In addition, to demonstrate the cytopathic effect of HCT-8 infected by HCoV-OC43 at an MOI of 0.05, the cells thus treated were stained with crystal violet after fixation at 6 d.p.i.

Compounds 1-6 exhibited strong antiviral activity against HCoV-OC43 viruses, having $EC_{50}$ values ranging from 16 nM to 1.8 µM for HCoV-OC43 with a selectivity index from 610 to 5.3 (Table 2).

TABLE 2

| Compound | $EC_{50}$ (nM) | $CC_{50}$ (nM) | Selectivity index |
| --- | --- | --- | --- |
| 1 | 68.0 ± 2.7 | >10000 | >147 |
| 2 | 16.4 ± 4.7 | >10000 | >610 |
| 3 | 55.9 ± 6.2 | >10000 | >179 |
| 4 | 51.7 ± 6.1 | >10000 | >193 |
| 5 | 213 ± 62 | >10000 | >46.9 |
| 6 | 1892 ± 228 | >10000 | >5.3 |

[a]Data means ± S.D. from three independent experiments, each in duplicate (HCoV-OC43).
[b]$EC_{50}$: The values of 50% maximal effective concentration.
[c]$CC_{50}$: The values of 50% maximal cytotoxic concentration.

Notably, Compounds 1-3 each had a very high potency inhibiting HCoV-OC43 viruses. These three compounds were then evaluated for cytopathic effects at 6 d.p.i. and IFA at 3 d.p.i., followed by a subsequent end point assay and TCID50 determination to show inhibitory activities in a dose-dependent manner. In the end point assay, HTC-8 cells were infected with HCoV-OC43 viruses at a MOI of 0.05 for 72 hours to reach a viral yield of $10^7$ p.f.u./ml and then treated using one of Compounds 1-3 at a predetermined concentration. Compounds 1-3 each significantly blocked viral replication and decreased viral yields, resulting in a viral yield reduction by 7 orders of magnitude at a concentration between 30 nM and 300 nM. See FIG. 1.

Example 3: Inhibition of HCoV-229E Viruses

Compounds 1-3 were used to inhibiting HCoV-229E virus, another human coronavirus belonging to genus of the alpha-coronavirus.

HCoV-229E viral genome replication was examined by RT-PCR with specific primers against its open reading frame 1 ("ORF1") and ORF nucleocapsid ("ORFN"). See Yang et al., *Front. Pharmacol.* 11, Article 606097 (2020).

Fetus lung fibroblast MRC5 cells were inoculated with the HCoV-229E virus at a MOI of 1. The MRC5 cells thus infected were treated with one of Compounds 1-3. Untreated MRC5 cells were used as a control sample. RT-PCR analysis was performed. Compounds 1-3 each inhibited HCoV-229E viral genome replication and subgenomic viral RNA syntheses at a concentration between 10 nM and 300 nM.

Cytopathic effects were studied and visualized after the infected cells were treated with one of Compounds 1-3. An end point assay by TCID50 was performed. Crystal violet was used to stain live cells to determine the $EC_{50}$ of each compound. See Table 3. Further, $CC_{50}$ and selective index were calculated.

TABLE 3

| Compound | $EC_{50}$ (nM) | $CC_{50}$ (nM) | Selectivity index |
| --- | --- | --- | --- |
| 1 | 71.4 ± 13.2 | 6635 ± 578 | 93 |
| 2 | 6.5 ± 1.0 | 1712 ± 161 | 264 |
| 3 | 25.4 ± 3.1 | 7362 ± 288 | 290 |

Data means ± S.D. from three independent experiments, each in duplicate (HCoV-229E).
$EC_{50}$: The values of 50% maximal effective concentration.
$CC_{50}$: The values of 50% maximal cytotoxic concentration.

HCoV-229E viral yield was studied following the procedure described above. Compounds 1-3 each significantly blocked viral replication and abolished the viral yield, resulting in a reduction of viral yield by 6~7 orders of magnitude at concentrations in the range of 30 nM to 600 nM in HCoV-229E infected MRC5 cells.

Example 4: Inhibition of Zika Virus

Compounds 1-9 were evaluated for their inhibitory activities against Zika virus using an IFA assay, which targeted Zika virus Envelope ("E") protein.

Vero E6 cells (BCRC #60476, Bioresource Collection and Research Center, Hsinchu, Taiwan) were treated with one of Compounds 1-9 at a predetermined concentration for 1 hour at 37° C. The cells were adsorbed with Zika virus (ATCC VR-1843, American Type Culture Collection, Manassas, VA, USA) at MOI=0.02 for 49 hours at 37° C. The cells were fixed with 10% formalin, permeabilized with methanol. The cells were stained with anti-flavivirus E antibody (ATCC HB-112, American Type Culture Collection, Manassas, VA, USA) and anti-mouse IgG-FITC (MP Biomedicals, Irvine, CA, USA). The nuclei were counter stained with DAPI (in blue) (Thermo Fisher Scientific, MA, USA). The E protein expression was measured using a high-content image analysis system (Molecular Devices). The cell viability was determined by MTS. Both $EC_{50}$ and $CC_{50}$ were calculated by Prism software.

Their cytotoxic effects were also determined by the MTS assay described above using Vero E6 cells. Each of Compounds 1-9 effectively inhibited Zika virus. On the other hand, their 50% cytotoxic concentrations were much higher than their $EC_{50}$, indicating a high selectivity of inhibiting Zika virus. The results were shown in Table 4 below.

TABLE 4

| Compound | $EC_{50}$ (nM) | $CC_{50}$ (nM) |
| --- | --- | --- |
| 1 | 61.4 | >5000 |
| 2 | 15.3 | >5000 |
| 3 | 15.9 | >5000 |
| 4 | 13.3 | >5000 |
| 5 | 156 | >5000 |
| 6 | 1036 | >5000 |
| 7 | 44.4 | >5000 |
| 8 | 304 | >5000 |
| 9 | 144 | >5000 |

Example 5: Inhibition of Dengue Virus

Compounds 1-9 were evaluated for their inhibitory activities against Dengue virus, another single positive-stranded RNA virus belonging to genus of flavivirus, using an IFA assay that targeted the Dengue virus Envelope ("E") protein.

Vero E6 cells (BCRC #60476, Bioresource Collection and Research Center, Hsinchu, Taiwan) were treated with one of Compounds 1-9 at a predetermined concentration for 1 hour at 37° C. The cells were infected with Dengue virus type 1 ("DV1", ATCC VR-1856, American Type Culture Collection, Manassas, VA, USA) at MOI=0.002 or Dengue virus type 2 ("DV2", ATCC VR-1584, American Type Culture Collection, Manassas, VA, USA) at MOI=0.02, both for 5 days at 33° C. They were then fixed with 10% formalin and permeabilized with methanol. Subsequently, the cells were stained with anti-flavivirus E antibody (ATCC HB-112, American Type Culture Collection, Manassas, VA, USA) and anti-mouse IgG-FITC (MP Biomedicals, Irvine, CA, USA). The nuclei of the cells were counter stained with DAPI (Thermo Fisher Scientific, MA, USA). The E protein expression was measured by using a high-content image analysis system (Molecular Devices). The cell viability was determined by MTS. EC50 and CC50 were calculated by Prism software.

Compounds 1-9 each were highly effective in inhibiting dengue virus. See Table 5 below.

TABLE 5

| compound | DV1 $EC_{50}$ (nM) | DV2 $EC_{50}$ (nM) | Vero E6 $CC_{50}$ (nM) |
|---|---|---|---|
| 1 | 18.4 | 32.5 | >5000 |
| 2 | 4.3 | 4.7 | >5000 |
| 3 | 19.6 | 29 | >5000 |
| 4 | 7.6 | 8.3 | >5000 |
| 5 | 131 | 286 | >5000 |
| 6 | 1638 | 2641 | >5000 |
| 7 | 73.1 | 124 | >5000 |
| 8 | 247 | 617 | >5000 |
| 9 | 296 | 616 | >5000 |

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for inhibiting a positive strand RNA virus, the method comprising:
   identify a subject infected with the positive strand RNA virus, and
   administering to the subject an effective amount of a compound of Formula II:

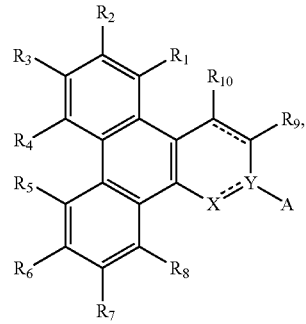

Formula II wherein
each of $R_1$, $R_2$, $R_3$, $R_4$, $R_5$, $R_6$, $R_7$, $R_8$, $R_9$, and $R_{10}$, independently, is H, alkyl, alkenyl, alkynyl, cycloalkyl, heterocycloalkyl, aryl, heteroaryl, halo, nitro, cyano, —$OR^a$, —$OC(O)R^a$, —$C(O)OR^a$, —$NR^aR^b$, —$NR^aC(O)R^b$, or —$C(O)NR^aR^b$, each of $R^a$ and $R^b$, independently, being H, alkyl, aryl, heteroaryl, cycloalkyl, or heterocycloalkyl;

X⸺Y, together, is C(R')(R")—N or CR'=N⁺, in which R' is H, alkyl, alkenyl, alkynyl, cycloalkyl, heterocycloalkyl, aryl, heteroaryl, halo, nitro, or cyano, and R" is H, alkyl, alkenyl, alkynyl, cycloalkyl, heterocycloalkyl, aryl, heteroaryl, halo, nitro, cyano, —$OR^c$, or —$OC(O)R^c$, $R^c$ being H, alkyl, aryl, heteroaryl, cycloalkyl, or heterocycloalkyl;

A is H, alkyl, alkenyl, alkynyl, cycloalkyl, heterocycloalkyl, aryl, or heteroaryl;

⸺ is a single bond or a double bond; and the positive strand RNA virus is a Zika virus or a Dengue virus.

2. The method of claim 1, wherein each of $R_1$, $R_4$, $R_5$, and $R_8$ is H; $R_2$ is H or alkoxy; each of $R_3$, $R_6$, and $R_7$, independently, is alkoxy; $R_9$ is H or alkyl, $R_{10}$ is H or OH; X is $CH_2$; Y is N; A is alkyl; and ⸺ is a single bond.

3. The method of claim 2, wherein the compound of Formula II is selected from the group consisting of Compound 2, Compound 3, Compound 5, Compound 7, Compound 8, and Compound 9:

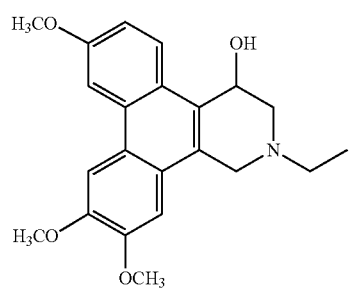

2

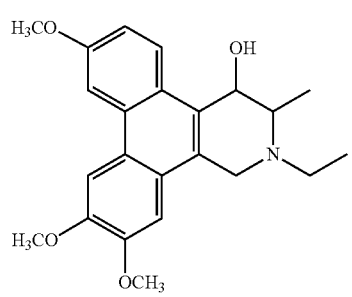
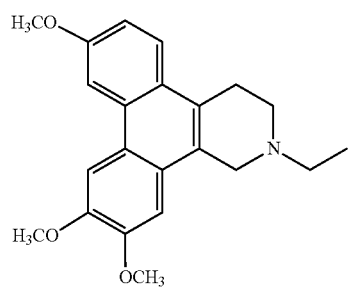
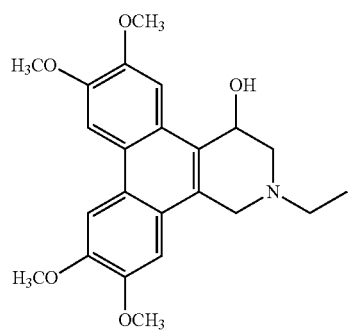
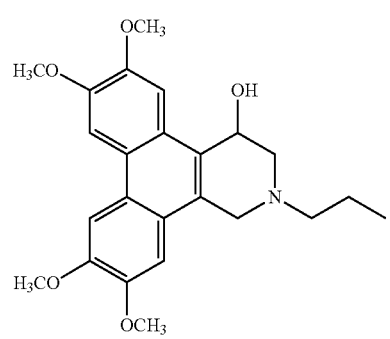
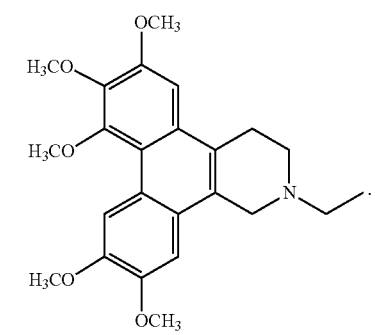
* * * * *